(12) United States Patent
Schröder

(10) Patent No.: US 6,544,496 B1
(45) Date of Patent: *Apr. 8, 2003

(54) DIAGNOSTIC AND CONTRAST AGENT

(75) Inventor: Ulf Schröder, Lund (SE)

(73) Assignee: Amersham Health AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 08/481,131

(22) Filed: Jun. 7, 1995

Related U.S. Application Data

(63) Continuation of application No. 08/361,466, filed on Dec. 22, 1994, now Pat. No. 5,618,514, which is a continuation of application No. 08/186,096, filed on Jan. 25, 1994, now abandoned, which is a continuation of application No. 08/043,982, filed on Apr. 7, 1993, now abandoned, which is a continuation of application No. 07/888,305, filed on May 27, 1992, now abandoned, which is a continuation of application No. 07/693,031, filed on Apr. 30, 1991, now abandoned, which is a continuation of application No. 07/278,326, filed on Nov. 30, 1988, now abandoned, which is a continuation of application No. 06/775,047, filed on Aug. 15, 1985, now abandoned.

(30) Foreign Application Priority Data

Dec. 21, 1983 (SE) .............................................. 8307060

(51) Int. Cl.⁷ .................................................. A61B 8/13
(52) U.S. Cl. ............................ 424/9.5; 514/54; 514/57; 514/59; 600/441; 600/458
(58) Field of Search ........................ 424/9.5, 646, 648, 424/9.322; 514/6, 54, 57, 59; 128/662.02; 436/173; 423/632, 633; 324/248

(56) References Cited

U.S. PATENT DOCUMENTS

| | | | |
|---|---|---|---|
| 3,663,687 A | 5/1972 | Evans | 424/1 |
| 3,720,761 A | 3/1973 | Hunter | 424/1.1 |
| 3,832,457 A | 8/1974 | Sugimoto et al. | 424/4 |
| 3,932,805 A | 1/1976 | Abe et al. | 424/9 |
| 4,101,435 A | 7/1978 | Hasegawa et al. | 252/62.53 |
| 4,247,406 A | 1/1981 | Widder et al. | 252/62.53 |
| 4,265,251 A | 5/1981 | Tickner | 128/660 |
| 4,276,885 A | 7/1981 | Tickner | 128/660 |
| 4,331,654 A | 5/1982 | Morris | 424/38 |
| 4,442,843 A | 4/1984 | Rasor et al. | 128/660 |
| 4,452,773 A | 6/1984 | Molday | 424/1.1 |
| 4,501,726 A | 2/1985 | Schroder et al. | 424/1.1 |
| 4,572,203 A | 2/1986 | Feinstein | 128/661 |
| 4,615,879 A | 10/1986 | Runge et al. | 424/9 |
| 4,657,756 A | 4/1987 | Rasor et al. | 424/9 |
| 4,675,173 A | 6/1987 | Widder | 424/9 |
| 4,681,119 A | 7/1987 | Rasor et al. | 128/660 |
| 4,718,433 A | 1/1988 | Feinstein | 128/660 |
| 4,731,239 A | 3/1988 | Gordon | 424/9 |
| 4,774,958 A | 10/1988 | Feinstein | 128/660.01 |
| 4,827,945 A | 5/1989 | Groman et al. | 128/653.4 |
| 4,900,540 A | 2/1990 | Ryan et al. | 424/9 |
| 5,141,738 A | 8/1992 | Rasor et al. | 424/2 |

FOREIGN PATENT DOCUMENTS

| | | | |
|---|---|---|---|
| AU | 86 330/82 | 1/1983 | |
| EP | 0 136 812 | 8/1984 | |
| GB | 1174366 | 4/1968 | A61K/27/08 |
| GB | 2137612 A | 1/1984 | C07C/101/02 |
| WO | WO78/00005 | 12/1978 | A61K/9/00 |
| WO | 80/02365 | 11/1980 | |
| WO | WO83/03426 | 3/1983 | C12N/5/00 |
| WO | WO83/01738 | 5/1983 | |
| WO | WO83/03920 | 11/1983 | H01F/1/09 |
| WO | WO84/02643 | 7/1984 | |
| WO | WO85/04330 | 3/1985 | A61K/49/00 |

OTHER PUBLICATIONS

Abe et al., "Development Procedure of Magnetic Focusing Method for NMR Medical Application," vol. 2, No. 1, pp. 1–23, 1984.
Cox et al., *J. Pharm. Pharmac.*, 24, 1972, 513–517.
Ohgushi et al., *Journal of Magnetic Resonance*, 29, 1978, 599–601.
Tanaka et al., *Sogo Rinsho*, 30:2609–2614, 1981, translated.
Tanaka et al., *Proceedings of the IEEE*, 66:1582–1583, 1978, translated.
Nakamura et al., *J. Applied Physics*, 42, 4, 1971, p. 1320.
Newbower, *IEEE Transections on Magnetics*, vol. Mag. 9, No. 3, Sep. 1973, pp. 447–450.
*NMR Imaging in Biomedicine*, Mansfield and Morris, Supp. 2, Advances in Magnetic Resonance, 1982, p. 234.
Runge et al., *Radiology*, 147, Jun. 3, 1983, p. 789 (Abstract).
Stark et al., *Radiology*, Sep. 1983, "Nuclear Magnetic Resonance Imaging of Experimentally Induced Liver Disease", pp. 743–750.
Becker, *High Resolution NMR*, Therory and Chemical Applications, 2nd Edition, 1980, p. 97.
Runge et al., *Intl. J. Nucl. Med. Bull.*, 12, 1, 1985, 37–42, "Particulate Oral NMR Contrast Agents".

*Primary Examiner*—Dameron L. Jones
(74) *Attorney, Agent, or Firm*—Kenyon & Kenyon

(57) ABSTRACT

The present invention relates to a method of contrast enhanced ultrasonic diagnostic imaging comprising administering to a subject a contrast enhancing amount of spherical particles comprising a matrix enclosing a gaseous contrast agent which reflects sound waves, said matrix being a biocompatible, biodegradable, non-immunogenic non-polyamino acid synthetic polymer; and generating an ultrasonic image of said subject. The polymer may be selected from the group consisting of carbohydrates, carbohydrate derivatives and non-polyamino acid synthetic polymers.

22 Claims, No Drawings

DIAGNOSTIC AND CONTRAST AGENT

This application is a Continuation of application Ser. No. 08/361.466. filed Dec. 22. 1994. now U.S. Pat. No. 5,618, 514 which is a continuation of abandoned application Ser. No. 08/186,096 filed Jan. 25, 1994, which is a continuation of abandoned application Ser. No. 08/043,982 filed Apr. 7, 1993, which is a continuation of abandoned application Ser. No. 07/888,305 filed May 27, 1992, which is a continuation of abandoned application Ser. No. 07/693,031 filed Apr. 30, 1991, which is a continuation of abandoned application Ser. No. 07/278,326 filed Nov. 30, 1988, which is a continuation of abandoned application Ser. No. 06/775,047 filed Aug. 15, 1985.

BACKGROUND

The invention relates to response particles, preferably spheres, and their use as a diagnostic and contrast agent.

In diagnostic medicine, contrast agents are today being used primarily in X-ray diagnostics where an increased contrast effect is obtained during examination of, for example, internal organs, such as the kidneys, the urinary tract, the digestive tract, the vascular system of the heart (angiography), etc. This contrast effect is based upon the fact that the contrast agent itself is less permeable to X-rays than the surrounding tissue, as a result of which a different blackening of the X-ray plate is obtained.

X-raying implies certain radiation hazards, but during angiography the complication risk is associated in particular with the use of contrast agents.

In recent years, a number of new methods have been introduced in diagnostic radiology. One such method goes by the name NMR (Nuclear Magnetic Resonance) which provides information not only about the distribution of the water content in a specific tissue (in contradistinction to radiology which merely gives a measure of the transmissibility of the X-rays in a specific tissue), but also about the chemical tissue structure which is different in normal and pathological tissue.

In the NMR method, a strong and homogeneous magnetic field is applied across the tissue to be examined. By studying the so-called relaxation times of the protons of the molecules present, especially the protons of the water, it is possible to produce, via comprehensive and complex computer calculations, a visual image of the structure of the tissue concerned.

There is, however, an interest in being able to make a differential diagnosis between pieces of tissue having a high density of blood vessels and, alternatively, tissue having a low density of vessels. Such a situation which has considerable clinical interest, comprises the localisation of tumours which, in their periphery, have a higher density of vessels as compared with normal tissue.

One useful method in the context is to inject into the vascular system some type of particles responsive to a magnetic field and showing changes in the above-mentioned relaxation times.

These magnetically responsive particles interfere with the above-mentioned homogeneous magnetic field in that there is formed, around each individual particle, a field gradient which in its turn changes the relaxation times.

Put more simply, this means that "black holes" are formed around each particle which may be visualised and thus give an impression of the vessel density in the tissue in question.

In another diagnostic method, use may be made of the movability of magnetically responsive particles in a tissue. The basic principle of this method may be studied according to the following: If magnetically responsive particle are introduced into a magnetic field, the particles will align themselves in the direction of the field lines. If the field is removed or shut down, the magnetically responsive particles will change their position in response to processes in the tissue. The duration of this change may, however, vary between different tissues and also in dependence upon the localisation of the particles within the tissue in question. This variability of the response of the magnetic material may be utilised diagnostically. If magnetically responsive particles are administered to a patient, the distribution of the particles in different organs can be determined by means of a sensitive magnetometer capable of detecting the above-mentioned changes (Nature (1983) 302, 336).

Ultrasonics is another visualisation technique in which sound-waves are reflected differently against different types of tissue, depending upon the acoustic impedance of these tissues. Also in this respect, there is an interest in being able to use some type of contrast agent in order to obtain an amplification of specific organs. Particles of different types have here been shown to provide changed echo effects and a changed resolution associated therewith (see, Edwards and Jarzynski, *J. Acoust. Soc. Am.,* 74:1006 (1983)). Edwards and Jarzynski studied ultrasound scattering by spherical microspheres which may contain gas, namely glass bubbles and hydrogen gas bubbles, and discussed future studies with liquid droplets. The present invention includes a sphere or particle for use in diagnostics or as a contrast agents which agent reflects sound waves and is characterized in that it consists of a matrix and the diagnostic and/or contrast agent enclosed within said matrix.

It is also possible to use magnetically responsive particles having a Curie point of about 42° C. for use at hyperthermia. In this instance, the magnetically responsive particles are retained during the treatment of the hyperthermia by a magnetic field, but the moment the tissue temperature exceeds the Curie point, the particles disappear from the tissue because the magnetic responsiveness disappears at this temperature.

By labelling the particles with some gamma-radiating nuclide (for example technetium-99m) it is possible to localise the particles by means of a gamma camera and thereby also to combine the examination with some of the other techniques referred to above.

When using particles within any of the above-mentioned ranges, it is desired, in order to achieve optimal conditions, to be able to vary the amount of magnetically or otherwise responsive material, without affecting on that account the pharmacodynamic and circulatory characteristics of the particles. To be able to do this, one must use a technique which implies enclosing the responsive material in a matrix, preferably a matrix of spherical shape, and the matrix should per se satisfy the following criteria:

biocompatible biologically degradable nonimmunogenic.

A matrix of this type normally is built up of some type of polymers which are held together by chemical bonds. Different types of polymers are available for making such matrices. However, the selection of polymers will be very limited if the above-mentioned criteria of the matrix are to be fulfilled.

One type of polymers that has proved useful in these contexts are the carbohydrates, especially those who are included in the body as a natural constituent.

Endogenous carbohydrates are represented by starch and glycogen, but also dextran may be included in this group because of its prolonged use as a blood substituent in medical service.

The production of a carbohydrate matrix satisfying these criteria is described in PCT/SE82/00381, which corresponds to U.S. Pat. No. 4,501,276, PCT/SE83/00106 which corresponds to U.S. Pat. No. 4,687,748, and PCT/SE83/00268 which corresponds to U.S. Pat. No. 4,713,249.

Another type of polymers that have proved to satisfy the said criteria are polyamino acids, such as proteins of the type albumin. The production of polyamino acid matrices is disclosed in U.S. Pat. No. 4,247,406.

Further types of polymers are represented by synthetic polymers, such as acrylates, polystyrene etc. The production of matrices from synthetic polymers is well documented in literature.

It is in this connection extremely advantageous if covalent cross-linking of the polymers can be avoided in the production of a useful matrix. For example, covalently cross-linked carbohydrate matrices have been found to produce transformed cells, in the form of granuloma, when used on humans (Am.Surg. (1955) 142, 1045).

When using covalently cross-linked proteins, there is a risk of immunological reactions because the resulting derivatised protein is not recognised by the body's immunity system as a protein belonging to the body. There are, however, for specific systems no alternatives to the covalent cross-linking, especially when using synthetic polymers or combinations of different polymers and cross-linking agents in order to obtain a useful system. As an example, it is possible to cross-link acrylic polymers with starch and, alternatively, to cross-link starch with acrylates.

Another useful possibility which is described in literature is the production of larger particles from smaller particles. For example, it is possible to produce, from 0.5 $\mu$m particles, conglomerates of larger particles, for example in the range of about 10 $\mu$m.

Another factor of importance to the injection of spheres into the vascular system is that the spheres have a size that prevents them from getting stuck in the capillary system of different tissues during the first passage. To prevent this, the particle must have a diameter below 1 $\mu$m (Chem.Pharm.Bull. (1975) 23, 1452) and a surface structure of hydrophilic character.

When particles are injected into the vascular system, all particles will have collected after a given period of time in the liver or spleen,(the RES system) because the normal function of these organs is to purify the blood of foreign particles. At present, there is only one method described which is capable of collecting particles to organs other than those mentioned above, and this is by utilising magnetically responsive particles or spheres.

This is of particular interest in the context of this invention because spheres containing magnetically responsive substances can be used and be made to stop in different tissues by means of the outer magnetic field. When the magnetically responsive particles then are stuck in the desired tissue, the tissue in question can simply be visualized by means of the NMR method or some of the other techniques referred to above.

DESCRIPTION OF THE INVENTION

The invention relates to responsive particles, preferably spheres, and their use as a diagnostic and contrast agent. The invention shows that it is possible to utilise spheres as contrast agents, the responsive material being enclosed within a matrix. The responsive material may consist of, for example, magnetite particles enclosed in the form of discrete particles of varying size, or in the form of complexed ions.

One conceivable matrix for use in the context of this invention consists of carbohydrates that have been stabilised by crystallization, which means that the type of chemical bonds holding the polymeric network together is not covalent in character, mainly hydrogen bonds, van der Waals forces or, in some cases, ion bonds.

As carbohydrate, use may be made of all conceivable variants, including carbohydrates of varying molecular weight and/or substituted or otherwise derivatised carbohydrates. For example, it may be mentioned that it is possible to produce and use magnetically responsive carbohydrate particles in which the carbohydrate is of starch origin and low-molecular of the type glucose, maltose, dextrins etc., and successively increasing molecular weight up to native potato starch having a molecular weight of several millions. The same molecular weight range is applicable to other carbohydrate groups, such as dextran or glycogen.

Another matrix for use in the complex of this invention may consist of polyamino acids, such as the protein albumin in which the matrix is stabilised by heating and the cohering forces are not covalent in character, of the type hydrophobic interactions, hydrogen bonds, van der Waals forces or ion bonds. In a manner similar to what has been stated above, it is also possible to use synthetic polymers or combinations as matrix.

The following Example should not be regarded as restrictive and merely serves to illustrate the main features of the invention.

EXAMPLE

Dextran spheres having a size of about 1 $\mu$m with enclosed magnetite particles (size 10–20 nm) were suspended in human serum. The relaxation times of the solution were measured with an NMR apparatus (Praxis II, Alnor Instrument AB, Nyköping) and compared with the relaxation times for the same serum without magnetically responsive dextran spheres. The following values of T1 and T2, respectively, were obtained.

|  |  | T1 (ms) | T2 (ms) |
|---|---|---|---|
| Serum without particles: |  | 1660 | 400 |
| Serum with particles: conc.: | 0.05 mg/ml | 1342 | 109 |
|  | 0.1 mg/ml | 1306 | 82.2 |
|  | 0.2 mg/ml | 1147 | 52.6 |
|  | 0.5 mg/ml | 968 | 30.7 |
|  | 1.0 mg/mi | 813 | 24.0 |
|  | 2.0 mg/ml | 688 | 19.9 |
|  | 4.0 mg/ml | 691 | 22.9 |

What is claimed is:

1. A method of contrast enhanced ultrasonic diagnostic imaging comprising: administering to a subject a contrast enhancing amount of spherical particles comprising a matrix of a biocompatible, biodegradable, non-immunogenic polymer enclosing a gaseous contrast agent which reflects sound waves, said polymer being selected from the group consisting of carbohydrates, carbohydrate derivatives and non-polyamino acid synthetic polymers; and generating an ultrasonic image of said subject.

2. The method of claim 1 wherein the matrix is of spherical shape.

3. The method of claim 1 wherein the matrix is stabilized by non-covalent bonds.

4. The method of claim 1 wherein the matrix comprises a polymer held together by chemical bonds.

5. The method of claim 1 wherein the matrix comprises a carbohydrate or carbohydrate derivative.

6. The method of claim 5 wherein the carbohydrate is endogenous.

7. The method of claim 5 wherein the matrix comprises glucose, maltose, sucrose, sorbitol or dextrin.

8. The method of claim 5 wherein the carbohydrate or carbohydrate derivative is a monosaccharide or a polysaccharide having two or more saccharide units.

9. The method of claim 8 wherein the carbohydrate comprises starch, glycogen or dextran.

10. The method of claim 4 wherein the polymer comprises a synthetic polymer.

11. The method of claim 10 wherein the synthetic polymer is selected from the group consisting of acrylates, polystyrene and derivatives thereof.

12. The method of claim 10 wherein the synthetic polymer is covalently crosslinked.

13. The method of claim 10 wherein the synthetic polymer comprises an acrylic polymer crosslinked with starch.

14. The method of claim 10 wherein the synthetic polymer comprises starch crosslinked with acrylates.

15. The method of claim 1 wherein the spherical or particles have a surface structure of hydrophilic character.

16. The method of claim 1 wherein the spherical or particles have a diameter in the range of 0.01–1000 $\mu$m.

17. The method of claim 1 wherein the spherical or particles have a diameter less than 1 $\mu$m.

18. The method of claim 1 wherein the particles are built up of conglomerates of smaller particles or spherical.

19. The method of claim 18 wherein the size of the conglomerates is about 10 $\mu$m.

20. The method of claim 18 wherein the size of the smaller particles or spheres is about 0.5 $\mu$m.

21. The method of claim 1 wherein an ultrasonic image is generated of the reticuloendothelial system, including the liver and spleen, of said subject.

22. The method of claim 1 comprising the further step of collecting particles to organs by additionally utilizing magnetically responsive particles or spheres and an outer magnetic field.

* * * * *

UNITED STATES PATENT AND TRADEMARK OFFICE
CERTIFICATE OF CORRECTION

PATENT NO. : 6,544,496 B1
DATED : April 8, 2003
INVENTOR(S) : Ulf Schroder

It is certified that error appears in the above-identified patent and that said Letters Patent is hereby corrected as shown below:

Title page,
Item [56], References Cited, OTHER PUBLICATIONS, change "Transections" to -- Transactions --.

Column 6,
Lines 3, 5 and 7, delete "or";
Line 9, change "the particles" to -- the spherical particles --;
Line 10, change "spherical." to -- spheres. --.

Signed and Sealed this

Second Day of September, 2003

JAMES E. ROGAN
*Director of the United States Patent and Trademark Office*